United States Patent [19]

Marsoner et al.

[11] Patent Number: 4,512,953

[45] Date of Patent: Apr. 23, 1985

[54] ANALYZING APPARATUS FOR THE ANALYSIS OF LIQUID SAMPLES

[75] Inventors: Hermann Marsoner; Christoph Ritter, both of Graz; Erich Kleinhappl, Kumberg; Winfried Strutz, Graz, all of Austria

[73] Assignee: AVL AG, Schaffhausen, Switzerland

[21] Appl. No.: 380,874

[22] Filed: May 21, 1982

[30] Foreign Application Priority Data

May 25, 1981 [AT] Austria .................................. 2343/81

[51] Int. Cl.³ ...................... G01N 35/00; G01N 35/08
[52] U.S. Cl. .................................... 422/67; 73/864.21;
 73/864.81; 422/63; 422/68; 422/81; 422/82;
 436/50; 436/52; 436/53
[58] Field of Search ....................... 422/63, 65, 67, 68,
 422/81, 82; 436/52, 53, 50, 47;
 73/864.21-864.25, 864.81

[56] References Cited

U.S. PATENT DOCUMENTS

| 4,253,846 | 3/1981 | Smythe et al. | 436/63 |
| 4,283,262 | 8/1981 | Cormier et al. | 422/81 X |
| 4,315,754 | 2/1982 | Ruzicka et al. | 422/81 X |
| 4,318,885 | 3/1982 | Suzuki et al. | 422/68 |
| 4,338,280 | 6/1982 | Ambers et al. | 422/81 X |
| 4,472,354 | 9/1984 | Passell et al. | 422/81 |

*Primary Examiner*—Michael S. Marcus
*Assistant Examiner*—Robert J. Hill, Jr.
*Attorney, Agent, or Firm*—Watson, Cole, Grindle & Watson

[57] ABSTRACT

An analyzing apparatus for the analysis of liquid samples is provided with a single sample input unit and a serial sample input unit which may alternatively be connected to a joint evaluation unit by means of a change-over switch. This will permit the measurement of single samples during a serial sample run by interrupting the automated process, additional provisions ensuring an automatic return to the serial sample mode.

3 Claims, 1 Drawing Figure

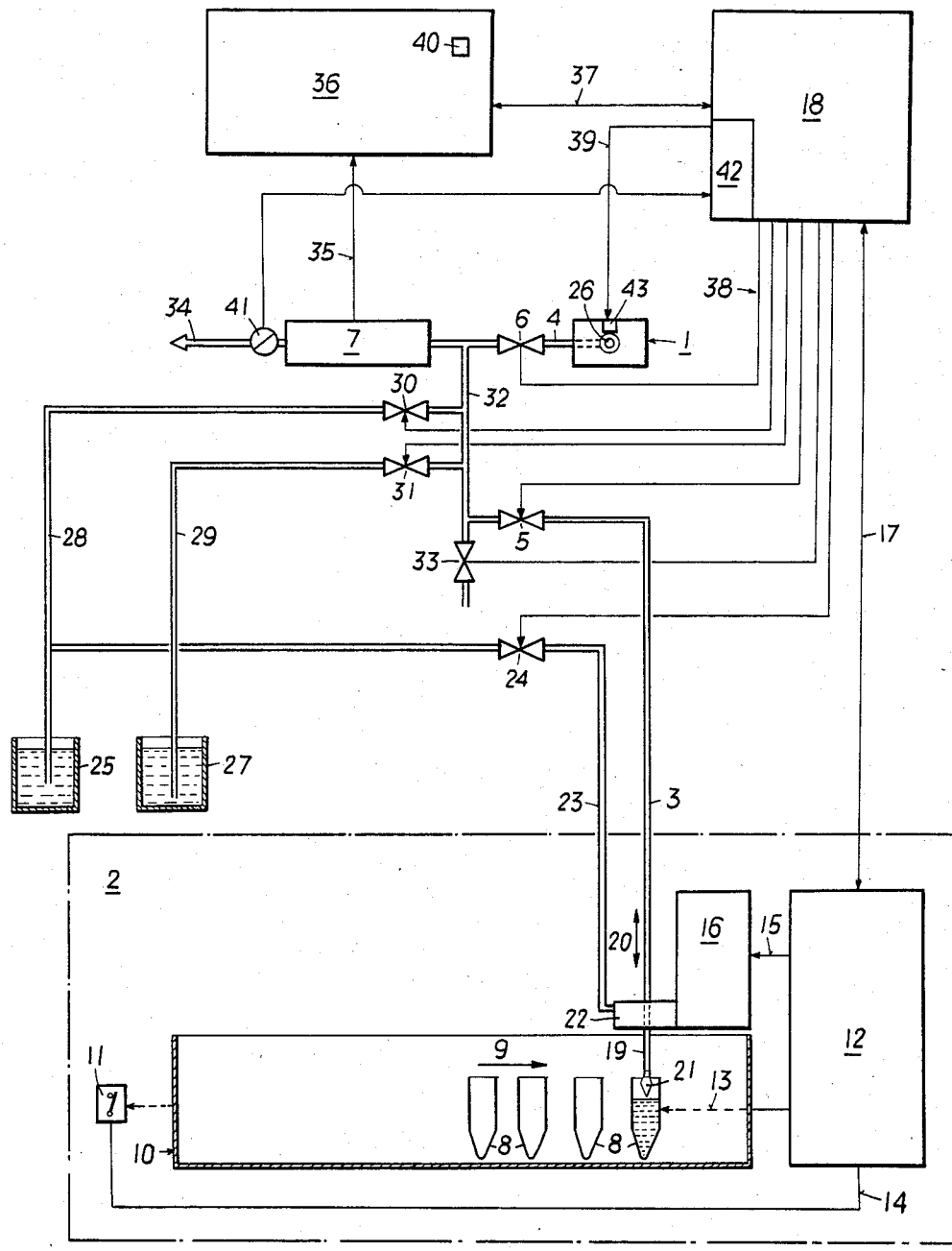

ANALYZING APPARATUS FOR THE ANALYSIS OF LIQUID SAMPLES

BACKGROUND OF THE INVENTION

The present invention relates to a chemical analyzer mainly used for the analysis of liquid samples, comprising a sample input device for introducing samples into an analysis path, and an evaluation unit for the measuring and display of measurement results.

DESCRIPTION OF THE PRIOR ART

Such analyzers may be found, e.g., in medical laboratories where they are used for blood gas analysis and other tests of liquid samples. According to the particular type of sample feed, known analyzers may be classified as apparatuses permitting the separate measuring of single samples to be introduced one by one only, the analyzer being ready to accept a new sample only after measuring of the previous sample has been completed, and as apparatuses permitting the automatic measuring of a sample series, in which case the test samples will only have to be entered into a feeder of the sample input device by the operating personnel while any further processing will be done automatically or will be controlled by the analyzer itself.

These two types of analyzers, which differ mainly with regard to the sample input, have certain disadvantages: (a) in the case of single sample input, the process of measuring similar samples of one series one by one is rather time-consuming and requires a separate operator, and (b) in the case of analyzers with input units for sample series, considerable operating efforts may be required if single samples are to be inserted into the analysis path, thereby interrupting the current serial measurements.

SUMMARY OF THE INVENTION

It is an object of the present invention to improve an analyzer of the aforementioned type in such a way as to avoid the above disadvantages of the known varieties in a simple manner.

According to the invention this is achieved by a sample input device comprising units for both single sample input and serial sample input which may be connected to a joint evaluation unit as required. In this way the advantages of both types of sample input units are combined and incorporated into one device while avoiding the drawbacks adhering to each type alone. The possibility of connecting either input unit to a joint evaluation unit eliminates the need for separate complicated and therefore expensive evaluation units for the two different types of sample input, which will reduce the cost of an analyzer combining all the advantages of the individual types in a simple manner.

In an enhanced version of the invention provisions are made for a switch at a central control unit permitting both interruption of the sample input when the analyzer is in the serial sample mode and a switch-over of the sample input to the single sample input unit upon the arrival of a signal from a sensor placed in the analysis path and sensing the passage of a sample, which sensor will indicate the completion of measuring those serial samples which had been entered into the analysis path but had not yet been measured at the time of switch-over. In this simple manner the actuation of the switch during a serial sample run will cause the serial samples already entered into the analysis path—and those only—to be fully processed before the evaluation unit is ready for measuring a single sample to be introduced via the single sample input unit. It may be useful to place the sensor sensing the passage of a sample behind the measurement electrodes in the analysis path, which means that the signal issued by this sensor for a switch-over to the single sample input unit will be received upon termination of the current serial sample measurements, but not before.

According to another proposal of the invention provisions may be made at the central control unit for a timing element which may be started by means of the sensor in the analysis path as soon as the measuring of an inserted single sample has been completed, and which may be reset if another sample is entered into the single sample input unit—as is indicated by another sensor located at the single sample input unit—and which will switch over the sample input device to the serial sample input unit on running down. In this way the analyzer will automatically return to the serial sample mode as soon as the inserted single sample has been measured, unless another single sample has been entered into the single sample input unit within a certain time defined by the timing element.

DESCRIPTION OF THE DRAWING

Following is a more detailed description of a preferred embodiment of the invention as illustrated by the enclosed drawing.

The analyzer shown in the enclosed diagram essentially comprises a sample input device and an evaluation unit measuring the liquid samples entered via the sample input device and delivering the respective measurement values.

The sample input device consists of both a single sample input unit 1 and a serial sample input unit 2, either of which may be connected to an evaluation unit common to both input units, especially to the measurement capillaries 7, by way of sample pipe 3, 4 and controlled valves 5, 6.

The serial sample input unit 2 is provided with a device (not shown in detail) for the automatic conveyance of sample bulbs 8 in the direction of the arrow 9, which is placed in a drawer 10 of the analyzer (only indicated schematically in this drawing) and has a switch 11 triggering the beginning of sample pick-up as soon as the drawer 10 is closed. A sample pick-up control unit 12 is provided with a recognition unit 13 for sample bulbs and liquid levels, and with connecting terminals for the signal line 14 from switch 11, and 15 from the needle transport mechanism 16, and 17 from the central control unit 18 of the analyzer.

In obeyance to control commands from the sample pick-up control unit 12, or rather from the central control unit 18, the needle transport mechanism 16 will effect a movement of the needle 19 in the direction of the arrow 20; during this process the needle 19 dipping its point into the sample bulb 8 in order to pick up a sample is axially guided in a flush tray 22 in a manner not shown. The flush tray 22 has a connection pipe 23 which may be blocked by a controlled valve 24 or charged with standard solution from a storage vessel 25.

The single sample input unit 1 is provided with an input orifice 26 which may be designed so as to hold syringes or sample capillaries. In addition, this variant of the present invention is characterized by provisions for a second storage vessel 27 for another standard solution, both vessels being linked to the measuring capillaries 7 via pipes 28, 29 as well as stop valves 30, 31 and a joint pipe 32. The joint pipe 32 is provided with an airing valve 33 which, when open, will permit the passage of air into the sample path, thus separating the individual sample batches from each other or from the standards.

At the end of the measuring capillaries 7 opposite the entry of the joint pipe 32 a suction line 34 is connected leading to a collecting vessel (not shown in this drawing) via a pump (also not shown).

The measuring capillaries 7 are connected to an evaluation unit 36 by one or several signal lines 35, which unit will also permit visual display or print-out of the measurement results, and which is connected to the central control unit 18 by a control line 37.

Finally, the function of the valves 5, 6, 30, 31, 33 and of the single sample input unit 1 itself may be controlled and monitored by the central control unit 18 via signal lines 38 and 39, respectively.

If the switch 40 directly mounted on the evaluation unit 36 in this variant is in the serial sample mode position and if the drawer 10 of the serial sample input unit has been closed, whereby switch 11 is actuated, the samples in the bulbs 8 controlled by the central control unit 18 are being measured automatically. For this purpose standard solution is being piped frm the storage vessel 25 into the flush tray 22 via pipe 23 and via the needle hole (not shown in this drawing) through the needle 19, the sample pipe 3 and the joint pipe 32 through the measuring capillaries 7. Afterwards, a separating air packet may be sucked in by dipping the needle hole below the flush tray 22. Following this, the needle 19 is lowered into the liquid sample contained in the bulb 8 and a predetermined amount of the liquid is drawn up into the analysis path. On termination of this process, after another air packet has been sucked in as described above, either a standard solution as before or another sample may be entered into the analysis path, after the bulbs 8 have been moved in the direction of arrow 9. The other standard solution in the storage vessel 27 is used for adjusting the analyzer with regard to another substance to be tested.

If a single sample is to be measured during the serial sample run, it will suffice in this context to actuate switch 40, which will interrupt the sample pick-up via the serial sample input unit 2. Measuring of those samples which have already entered the sample pipe 3 or the joint pipe 32 and which have been separated by standard solution or air packets, is continued in its usual manner until a sensor 41 which has been inserted, e.g., into suction pipe 34 behind the measuring capillaries 7 to sense the passage of the samples, will indicate completion of the measurement of those serial samples which have entered the analysis path but have not yet been measured at the time of actuation of the switch 40, and will switch the sample input device to the single sample input unit 1. A sample may be entered at the input orifice 26; pipes 28, 29 will convey the standard solution in a manner which is identical to that discussed in connection with the serial sample input.

In the variant under discussion the central control unit 18 is provided with a timing element 42 which is started by the sensor 41 as soon as the measuring of an inserted single sample has been completed. The input orifice 26 of the single sample input unit 1 is provided with another sensor 43 which is connected to the central control unit 18, or rather to the timing element 42 via the signal line 39, and which will reset the timing element 42 if another single sample is entered at the single sample input unit 1 within the time interval defined by the timing element 42. Provided that no further single sample has entered the orifice 26 by the time the timing element 42 has run down, the sample input device is switched back to the serial sample input unit 2 via the central control unit 18.

In this simple way the present invention will provide two different modes of sample input which will enable the analyzer to be used for a variety of purposes without involving any undue design efforts or cost.

We claim:

1. An analyzing apparatus for the analysis of liquid samples which comprises
   a measuring means for measuring properties of liquid samples supplied thereto and for providing measurement signals representative of the measured properties,
   an evaluation unit to which said measurement signals are fed, said evaluation unit acting to evaluate said measurement signals and display the evaluated results,
   a sample input device, said sample input device including a single sample input unit and a serial sample input unit,
   a first sample pipe connected between said single sample input unit and said measuring means for conveying single liquid samples from said single sample input unit to said measuring means,
   a first control valve located in said first sample pipe,
   a second sample pipe connected between said serial sample input unit and said measuring means for conveying liquid samples from said serial sample input unit to said measuring means,
   a second control valve located in said second sample pipe,
   a central control unit connected to said first control valve and to said second control valve,
   a switch means connected to said central control unit, and
   a first sensor positioned downstream of said measuring means for sensing the passage of each liquid sample through said measuring means and concurrently sending a corresponding first signal to said central control unit,
   said central control unit having a first operative mode wherein it generates a second and third signal to respectively close said first control valve and open said second control valve to allow only liquid samples from said serial sample input unit to pass to said measuring means and a second operative mode wherein it generates a fourth and fifth signal to respectively close said second control valve and open said first control valve to allow only liquid samples from said single sample input unit to pass to said measuring means, and said switch means, when activated, generates a sixth signal to activate said central control unit to generate a seventh signal to stop the placing of liquid samples from said serial sample input unit into said second sample pipe and to change from said first operative mode to said second operative mode when said central control unit receives an eighth signal from said first sensor that all liquid samples which were in said second sample pipe when said switch means was activated have passed said measuring means.

2. An analyzing apparatus as defined in claim 1, wherein said serial sample input unit includes means for simultaneously containing a plurality of sample containers, each sample container containing a separate liquid sample, and means for sequentially withdrawing a quantity of the liquid sample in each of said sample containers and placing it in said second sample pipe.

3. An analyzing apparatus as defined in claim 1, wherein said first sensor generates a ninth signal indicative that a single sample has past said measuring means, said analyzing apparatus further including a second sensor operatively associated with said single sample input unit to sense when a liquid sample has been placed therein and concurrently generating a tenth signal which is sent to said central control unit, wherein said central control unit includes a countdown timing element which receives said ninth and tenth signals from said first and second sensors, said countdown timing element starting its countdown once said central control unit has been changed to its second mode of operation by said switch means and said eighth signal from said first sensor and causing said central control unit to change to its first operative mode once its countdown reaches zero, the countdown of said countdown timing element being reset each time a signal from said second sensor is received.

* * * * *